United States Patent
Viitala et al.

(10) Patent No.: US 8,123,672 B2
(45) Date of Patent: Feb. 28, 2012

(54) BLOOD VESSEL PREPARATION AND PRESERVATION KIT

(75) Inventors: Daniel W. Viitala, Dexter, MI (US); Randal James Kadykowski, South Lyon, MI (US)

(73) Assignee: Terumo Cardiovascular Systems Corporation, Ann Arbor, MI (US)

(*) Notice: Subject to any disclaimer, the term of this patent is extended or adjusted under 35 U.S.C. 154(b) by 615 days.

(21) Appl. No.: 12/349,044

(22) Filed: Jan. 6, 2009

(65) Prior Publication Data
US 2009/0112053 A1  Apr. 30, 2009

Related U.S. Application Data

(63) Continuation-in-part of application No. 11/493,319, filed on Jul. 26, 2006, now abandoned.

(51) Int. Cl.
*A61F 2/06* (2006.01)
(52) U.S. Cl. ........................................................ 600/36
(58) Field of Classification Search ............... 600/36; 623/1.1–1.54; 435/289.1–305.4
See application file for complete search history.

(56) References Cited

U.S. PATENT DOCUMENTS

| | | | |
|---|---|---|---|
| 3,056,408 A | 10/1962 | Brown | |
| 3,911,926 A | 10/1975 | Peters | |
| 3,916,874 A | 11/1975 | Perrin | |
| 4,144,744 A | 3/1979 | Hill | |
| 4,157,179 A | 6/1979 | Ecklor, Jr. | |
| 4,232,659 A | 11/1980 | Dale | |
| 4,323,072 A | 4/1982 | Rosenbluth et al. | |
| 5,282,812 A | 2/1994 | Suarez, Jr. | |
| 5,772,576 A | 6/1998 | Knighton et al. | |
| 5,902,228 A | 5/1999 | Schulsinger et al. | |
| 6,132,472 A | 10/2000 | Bonutti | |
| 6,278,079 B1 | 8/2001 | McIntyre et al. | |
| 7,736,366 B2* | 6/2010 | Abdelgany et al. | 606/86 R |
| 2003/0065247 A1 | 4/2003 | Yap et al. | |
| 2003/0130674 A1 | 7/2003 | Kasahara et al. | |
| 2005/0021122 A1* | 1/2005 | Eisenkolb | 623/1.1 |
| 2005/0027347 A1* | 2/2005 | Chobotov et al. | 623/1.13 |
| 2005/0159764 A1 | 7/2005 | Kasahara et al. | |
| 2008/0169214 A1 | 7/2008 | Genovesi | |

FOREIGN PATENT DOCUMENTS

WO   WO2004086490   7/2004

* cited by examiner

*Primary Examiner* — Charles A Marmor, II
*Assistant Examiner* — Catherine E Burk
(74) *Attorney, Agent, or Firm* — Gael Diane Tisack, Esq.; Darryl Newell; MacMillan, Sobanski & Todd, LLC

(57) ABSTRACT

A vessel preparation and preservation kit supports a blood vessel during processing for use in bypass graft surgery. The device comprises a clamshell base having first and second trays latchable in a closed condition and pivotable to an open condition. The first tray has a series of open slots on an interior surface, wherein each slot extends substantially transverse to the longitudinal axis of the clamshell base. A first fixture has a first plate positionable in any selected one of the slots, a first fitting for holding a first end of the blood vessel, and a fluid supply needle for inserting into the first end of the blood vessel. A second fixture has a second plate positionable in any selected one of the slots a predetermined distance from the first fixture and having a second fitting for holding a second end of the blood vessel. A liquid-retaining foam is mounted in the second tray to immerse the prepared blood vessel in liquid to preserve it by putting the trays in the closed condition.

16 Claims, 4 Drawing Sheets

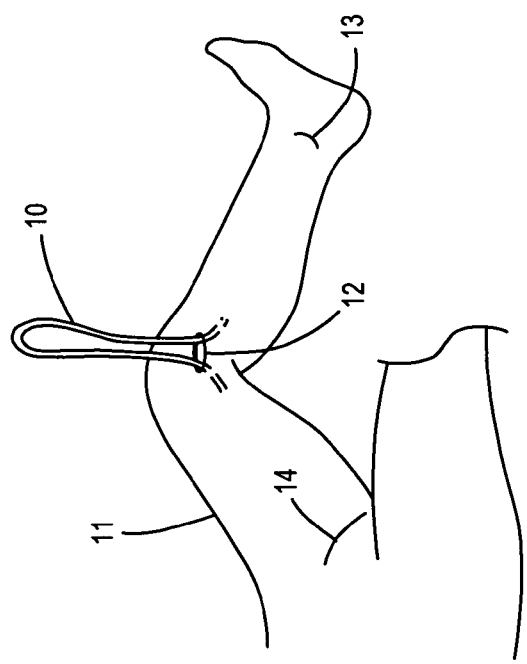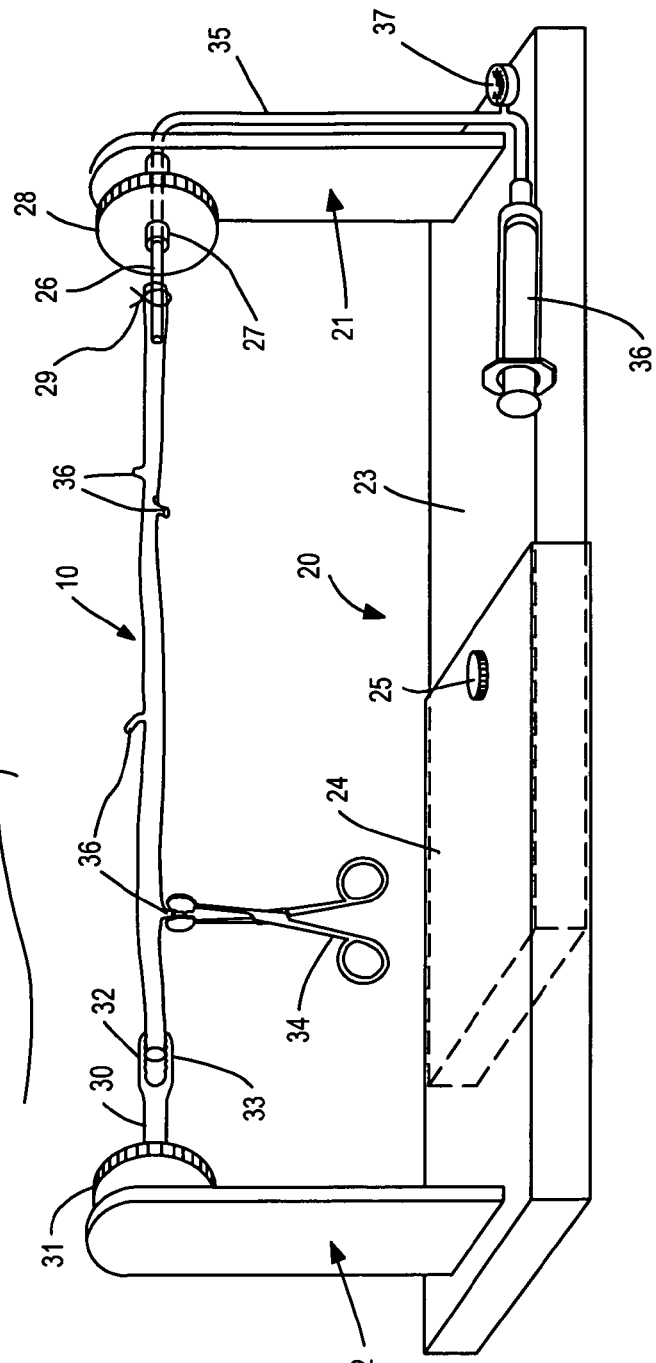

US 8,123,672 B2

BLOOD VESSEL PREPARATION AND PRESERVATION KIT

CROSS REFERENCE TO RELATED APPLICATIONS

This application is a continuation-in-part of application Ser. No. 11/493,319, filed Jul. 26, 2006, entitled "Device for Processing Blood Vessel Harvested for Bypass Graft Surgery," which is incorporated herein by reference in its entirety.

STATEMENT REGARDING FEDERALLY SPONSORED RESEARCH

Not Applicable.

BACKGROUND OF THE INVENTION

The present invention relates in general to a holder for a blood vessel harvested from a patient for use in cardiac bypass graft surgery, and, more specifically, to a device for assisting in sealing branch stubs and pressure testing of the blood vessel.

In coronary artery bypass grafting (CABG), a blood vessel or vessel section, such as an artery or vein, is "harvested" (i.e., removed) from its natural location in a patient's body for use elsewhere in the body. In CABG surgery, the blood vessel is used to form a bypass between an arterial blood source and the coronary artery that is to be bypassed. Among the preferred sources for the vessel to be used as the bypass graft are the saphenous veins in the legs and the radial artery in the arms.

Endoscopic surgical procedures for harvesting a section of a vein (e.g., the saphenous vein) subcutaneously have been developed in order to avoid disadvantages and potential complications of harvesting through a continuous incision (e.g., along the leg) for the full length of the desired vein section in order to provide adequate exposure for visualizing the vein and for introducing surgical instruments to sever, cauterize and ligate the tissue and side branches of the vein. One such minimally-invasive technique employs a small incision for locating the desired vein and for introducing one or more endoscopic harvesting devices. Primary dissection occurs by introduction of a dissecting instrument through the incision to create a working space and separate the vein from the surrounding tissue. Then a cutting instrument is introduced into the working space to sever the blood vessel from the connective tissue surrounding the section to be harvested and any side branches of the blood vessel. The branches may be clipped and/or cauterized.

In one typical procedure, the endoscopic entry site is located near the midpoint of the vessel being harvested, with dissection and cutting of branches proceeding in both directions along the vessel from the entry site. In order to remove the desired section of the blood vessel, a second small incision, or stab wound, is made at one end thereof and the blood vessel section is ligated. A third small incision is made at the other end of the blood vessel section which is then ligated, thereby allowing the desired section to be completely removed through the first incision. Alternatively, only the first two incisions may be necessary if the length of the endoscopic device is sufficient to obtain the desired length of the blood vessel while working in only one direction along the vessel from the entry point.

An example of a commercially available product for performing the endoscopic vein harvesting described above is the VirtuoSaph™ Endoscopic Vein Harvesting System from Terumo Cardiovascular Systems Corporation of Ann Arbor, Mich. Endoscopic vein harvesting systems are also shown in U.S. Pat. No. 6,660,016 to Lindsay and U.S. patent application publication 2005/0159764A1 in the name of Kasahara et al, both of which are incorporated herein by reference in their entirety.

After a vein is removed from the patient's body, it must be prepared for use as a bypass graft. Preparation includes ligating (i.e., closing off) each branch stub, injecting a solution into the vein under pressure to test for leaks, and otherwise inspecting the condition of the blood vessel. In the conventional procedures, branch stubs may be ligated using sutures for tying off each stub or staples may be employed for clamping off each stub. This processing of the blood vessel is normally performed by placing the blood vessel on a sterile surface over a patient's leg nearby the point from where it was harvested. Typically, two people (e.g., medical technicians, nurses) work together to hold the vein, apply a syringe of saline solution to pressurize the vessel, tie off or clip branch stubs as the vein is distended by the saline solution, and check for leaks. The prior art procedure is labor intensive and is difficult to perform on a loose, unsupported vein lying over an uneven surface. Since the amount of pressurized saline solution injected into a blood vessel is manually controlled according to the pressure being applied against a plunger of a syringe, the medical technician occasionally damages a blood vessel by over-pressurizing it. Other inadvertent damage may also occur during handling since the blood vessel is unrestrained and unprotected from other objects until such time as it is transferred to a bath of saline solution after it has been inspected by a surgeon performing the graft.

SUMMARY OF THE INVENTION

Among the benefits that can be realized according to different aspects of the invention are reduced labor and time for vessel preparation, safer application of pressurized saline solution when testing for leaks, better visualization for inspecting and measuring the vessel for surgical use, reliable protection of the vessel from accidental damage, and convenient immersion of the vessel in a bath for preservation until needed in the surgery, all provided by a disposable unit or kit.

In one aspect of the invention, a vessel holder supports a blood vessel during processing for use in bypass graft surgery. The holder comprises a base and a first fixture mounted on the base for holding a first end of the blood vessel. The first fixture has a fluid supply needle for inserting into the first end of the blood vessel. A second fixture is mounted on the base a predetermined distance from the first fixture for holding a second end of the blood vessel. The predetermined distance is adjustable for holding the blood vessel under tension.

BRIEF DESCRIPTION OF THE DRAWINGS

FIG. 1 shows a saphenous vein being removed from the leg of a patient following an endoscopic procedure.

FIG. 2 is a perspective view of one embodiment of a vessel holder according to the present invention.

DETAILED DESCRIPTION OF PREFERRED EMBODIMENTS

Figure 3:
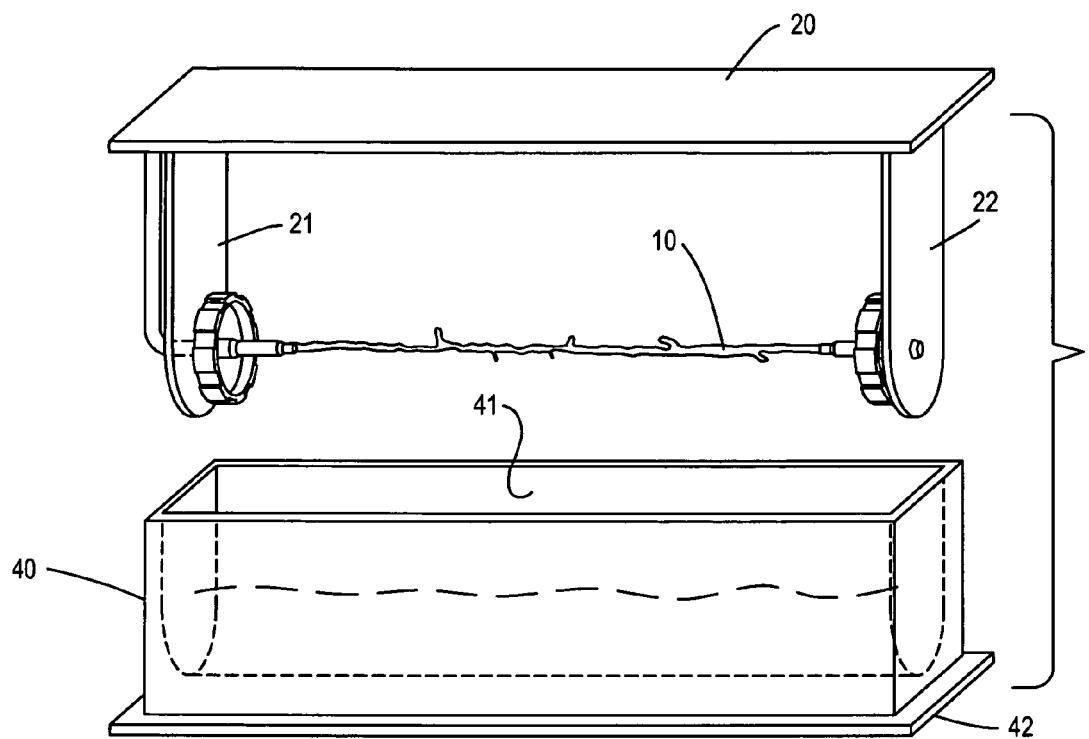
FIG. 3 is a perspective view of a further embodiment of the invention having a removable cover that is used to provide a bath.

The present invention provides a device for supporting a blood vessel during processing for use in bypass graft surgery. The vessel holder device comprises a base and first and second fixtures mounted on the base. The first fixture holds a first end of the blood vessel and has a fluid supply needle for inserting into the first end of the blood vessel. The second fixture holds a second end of the blood vessel at a predetermined distance from the first fixture. The predetermined distance between the first and second fixtures is adjustable so that the blood vessel is held under a desired amount of tension. By suspending the blood vessel with a gentle tension between the first and second fixtures, processing of a blood vessel can be performed by a single individual in a shorter period of time and with less damage to the blood vessel.

Referring now to FIG. 1, a saphenous vein 10 is being removed from a patient's leg 11 through an incision 12. During harvesting, main vessel 10 is severed from side branches extending from vessel 10 and then opposite ends of vessel 10 are cut at stab wounds 13 and 14 to free it for removal. The present invention may also be employed with blood vessels harvested using different surgical methods or from different areas of the patient's body.

The present invention may include a vessel holder device supplied as a disposable, sterile device for use by a physician's assistant or nurse to prepare a blood vessel. In a preferred embodiment, the device is constructed as a disposable stand molded from polycarbonate or other biocompatible material and using stainless steel attachment devices arranged to apply the necessary tension to the blood vessel to keep it taut in order to make tying or clipping of branch stubs easier than in the prior art wherein a loose blood vessel lies on an uneven leg surface. According to a first embodiment, the device in FIG. 2 includes a base 20 supporting a first fixture 21 and a second fixture 22 wherein base 20 includes interlocking pieces 23 and 24 to adjust the distance between fixtures 21 and 22. A locking mechanism of any known type such as a locking tab 25 is provided to maintain the desired predetermined distance according to the tension to be applied.

First fixture 21 includes a fluid supply needle 26 extending from a mounting boss 27 rotationally mounted to fixture 21. A rotation wheel 28 fixed to boss 27 allows for manual rotation of fluid needle 26 and boss 27. One end of blood vessel 10 is inserted over fluid supply needle 26 and is secured thereto by tying a suture 29 over the end of blood vessel 10 and tightening.

Second fixture 22 has a clamp 30 rotationally mounted thereon together with a rotation wheel 31. Clamp 30 has a pair of jaws 32 and 33 for grasping the end of blood vessel 10. With the first end of blood vessel 10 secured to needle 26, the distance between fixtures is adjusted (if need be) to a distance at which there is sufficient slack in vessel 10 to secure it to clamp 30. After attaching both ends of blood vessel 10, the length of base 20 is adjusted outward in order to provide a predetermined distance between fixtures 21 and 22 so that blood vessel 10 is held under a desired, gentle tension. With blood vessel 10 suspended between fixtures 21 and 22, each branch stub can be conveniently tied off or clipped by a single user. Blood vessel 10 can easily be reoriented by rotating it so that a desired branch stub is facing the user by moving rotation wheels 28 and 31 together. An additional manual clamp 34 may be attached to a branch stub during ligation to pull it perpendicularly away from the main vessel in order to make suturing easier.

Boss 27 and fluid supply needle 26 include a hollow passage coupled to a feed line 35 running from a syringe 36 mounted to base 20. Thus, saline solution from syringe 36 can be coupled through feed line 35, boss 27, and needle 26 to the interior of blood vessel 10. Saline solution or other fluid may be introduced into blood vessel 10 to gradually distend it along its length to each branch stub 36 for easier ligating of the branch stubs. In addition, fluid from feed line 35 is introduced into blood vessel 10 after completing all ligations in order to test them for leaks. In order to ensure that excessive pressures that may otherwise damage blood vessel 10 are not inadvertently introduced, a pressure gauge 37 is connected to feed line 35 allowing the user to monitor pressure being applied to the vessel and to maintain it at a safe level below a known threshold. Pressure gauge 37 is preferably adapted to be connected to an alarm generator (not shown) that compares the pressure with a threshold and produces an audible or visual alarm if the threshold is exceeded. The alarm generator may include a memory for storing pressure data for subsequent analysis.

FIG. 3 shows an optional enhancement to the embodiment of FIG. 2, wherein blood vessel 10 is maintained in a saline solution bath after the ligation and pressure testing steps. Thus, the vessel holder device may be flipped over and placed into a cover 45 having a reservoir 46 containing a sufficient depth of saline solution to immerse blood vessel 10 when the vessel holder is flipped over and inserted into reservoir 46. A flat block 47 may be provided at the bottom of cover 45 to maintain reservoir 46 in the upright position. Cover 45 may preferably be comprised of an injection molded polycarbonate or other biocompatible materials. Cover 45 and base 20 may fit together in a manner that preserves sterility during shipment from the point of manufacture to the point of use.

Figure 4:
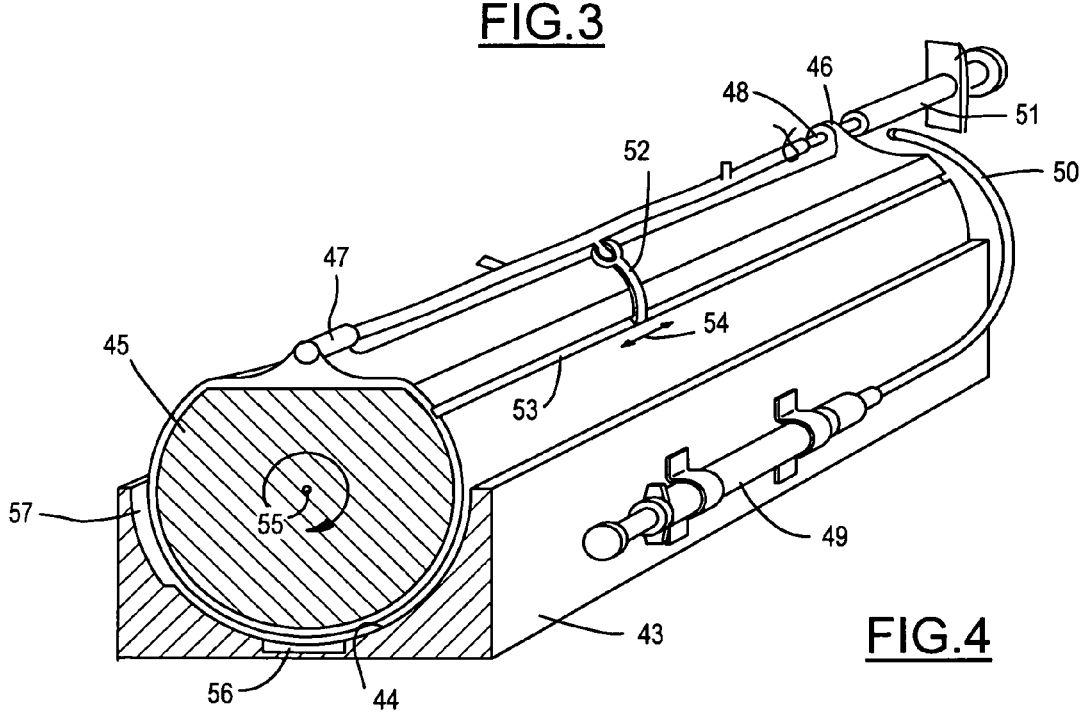
FIG. 4 is a cross-sectional perspective view according to another embodiment of the present invention.

FIG. 4 shows an alternative embodiment wherein a reservoir is incorporated into a base 43. Thus, base 43 includes a recess 44 for receiving a rotatable member 45 carrying a first fixture 46 for receiving blood vessel 10 and a swivel clamp 47 at the opposite end of member 45 for supporting the other end of blood vessel 10. A fluid supply needle 48 in first fixture 46 receives fluid from a syringe 49 and feed line 50 as described in the previous embodiment, or from an optional syringe 51 connected coaxially with needle 48. A branch clamp 52 is able to clamp branch stubs at its proximal end and is slidably mounted in a longitudinal groove 53 of member 45 at its proximal end. Clamp 52 can be slid back and forth in the direction shown by arrow 54 to coincide with branch stubs to be ligated.

After processing of blood vessel 10, rotatable member 45 may be rotated around its axis 55 so that after 180 degrees of rotation, blood vessel 10 resides in a bath chamber 56 running longitudinally at the bottom of recess 44 in base 43. Recess 44 may include a cut out area 57 to accommodate the space needed by branch clip 52 when member 45 is rotated to place blood vessel 10 into bath 56.

Figure 5:
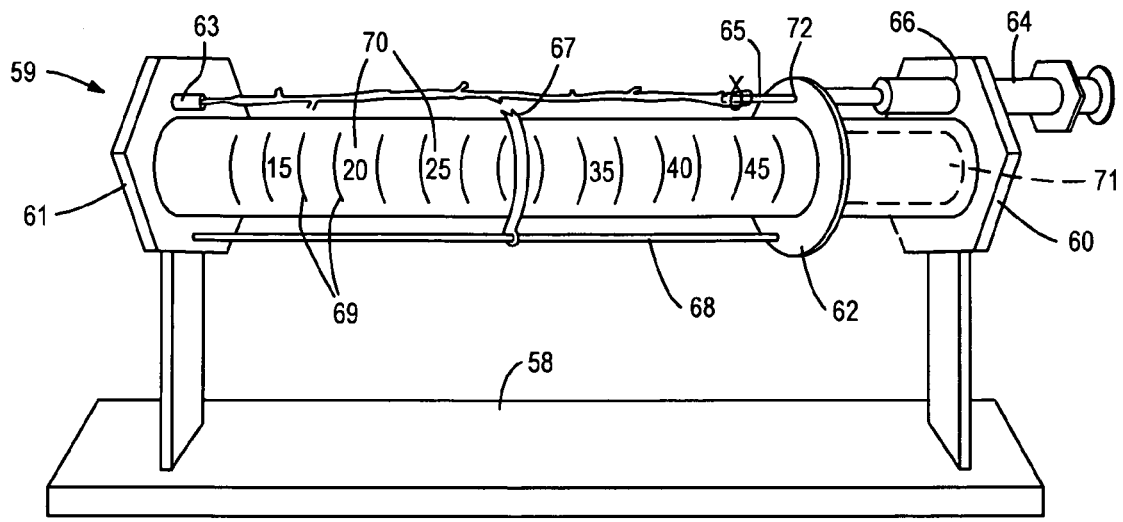
FIG. 5 is a perspective view of yet another embodiment of the vessel holder having graduation marks and labels for assisting in determining the length of a vessel being prepared.

FIGS. 5 shows yet another embodiment of a vessel holder. A base 58 supports a cylindrical tube member 59 having end flanges 60 and 61 and an intermediate flange 62. A clamp 63 is mounted to flange 61 for retaining one end of blood vessel 10. A syringe 64 extends through an aperture 66 in flange 60 and has a needle 65 extending through an aperture 72 in flange 62 to retain the other end of blood vessel 10. A snug but movable fit of syringe 64 in the apertures can provide an adjustable distance to achieve the desired tension in blood vessel 10. A branch clamp arm 67 is slidably mounted on a support rod 68 that extends between flanges 61 and 62.

Along the central tubular body of member 59, a plurality of graduations 69 are scribed or otherwise created at predetermined intervals. A plurality of labels 70 are also applied to member 59 to assist in determining the length of a vessel mounted to the vessel holder. Tube member 59 includes a cavity 71 for providing a bath for storing blood vessel 10 after processing.

Figure 6:
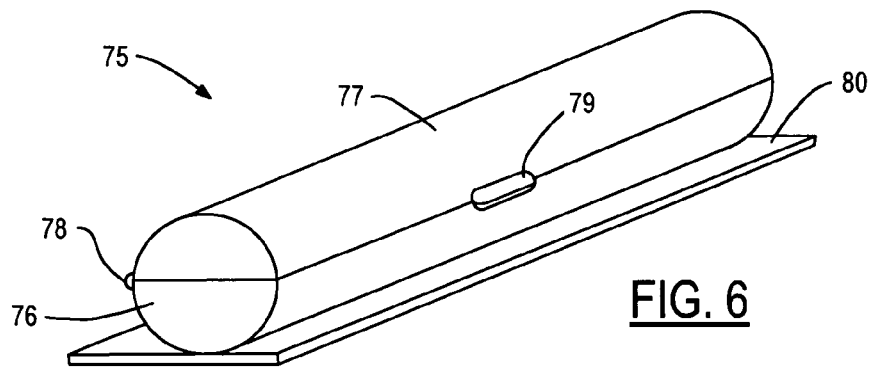
FIG. 6 is a perspective view of a vessel preparation and preservation kit according to yet another embodiment of the invention.
Figure 7:
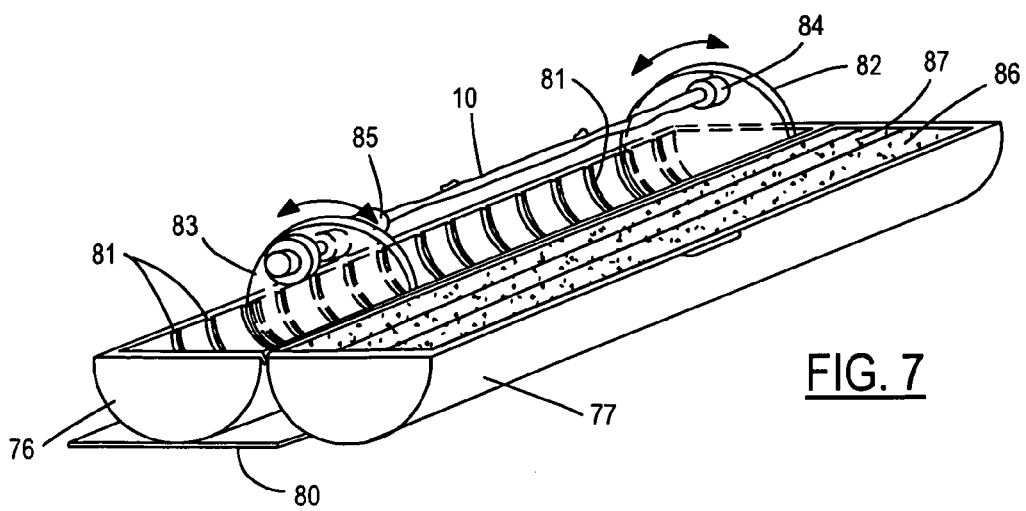
FIG. 7 is a perspective view of the kit of FIG. 6 in an opened position.

Yet another embodiment of a kit for preparing and preserving the harvested vessel is shown in FIGS. 6 through 10. In this embodiment, kit 75 includes a clamshell base having a first tray 76 and a second tray 77 joined by a longitudinal hinge 78 (e.g., a living hinge). A latch 79 with matching halves 79a and 79b latches trays 76 and 77 in a closed condition as shown in FIG. 6. Latch 79 is releasable so that trays 76 and 77 are pivotable around hinge 78 into an open condition as shown in FIG. 7. Preferably, the clamshell base may further include a bottom support 80 to stabilize it when closed. Trays 76 and 77, hinge 78, latch 79, and support 80 may preferably be integrally molded using a bio-compatible thermoplastic, such as nylon.

Kit 75 may be sold and shipped in the closed condition shown in FIG. 6 with all necessary components stored inside. When in the closed condition, trays 76 and 77 enclose a substantially cylindrical space that maintains sterility until opening.

As shown in FIG. 7, first tray 76 includes a series of open slots 81 on its inner semi-cylindrical surface that each extend transverse to the longitudinal axis of kit 75. Slots 81 are preferably evenly spaced along tray 76 and have a width adapted to receive a first fixture 82 in a selected slot and a second fixture 83 in another selected slot. Each fixture comprises a circular disc-shaped plate adapted to rotate in the respective slot 81. Fixture 82 includes a first fitting 84 for holding a first end of blood vessel 10, and fixture 83 has a second fitting 85 for holding a second end of blood vessel 10. Blood vessel 10 may be held under a desired tension by appropriately selecting the slots into which fixtures 82 and 83 are inserted. In addition to fixtures 82 and 83 being independently rotatable in their respective slots, fittings 84 and 85 are likewise independently rotatable on their respective plates so that blood vessel 10 can be placed into any desired rotation while it is being prepared.

Second tray 77 includes an open-cell foam 86 in a generally semi-cylindrically shaped body for retaining a preservation fluid that may be applied to vessel 10 following preparation (e.g., by closing the clamshell base to place vessel 10 into a longitudinal groove 87 in foam 86). Foam 86 may contain any preserving solution such as saline solution or a blood component. Preferably, the saline solution is introduced at the point of use after unsealing the kit. Any bio-compatible foam or sponge-like material can be employed, provided it is sufficiently rigid to easily be retained within tray 77.

Figure 8:
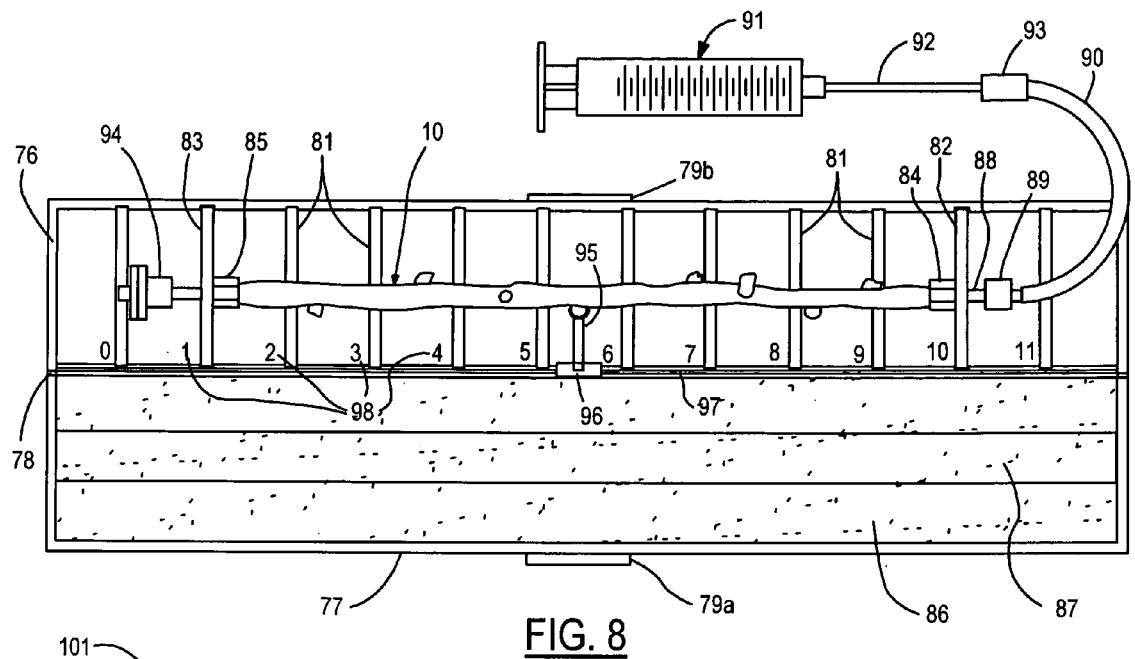
FIG. 8 is a top view of the kit in FIG. 7.

As best shown in FIG. 8, first fixture 82 further includes a fluid supply needle 88 passing through fitting 84 into blood vessel 10. A luer connection 89 couples fluid supply needle 88 to a fluid conduit 90 that is used to couple a source of pressurized solution to needle 88 so that the solution is injected into vessel 10 to perform leak and pressure testing. A syringe 91 that may be loaded with saline solution is coupled to fluid conduit 90 by a set 92 and pressure release valve 93 as in the previous embodiments. A hydrophilic filter 94 is provided on second fixture 83 in fluid communication with vessel 10 through fitting 85 in order to purge air via the second end of blood vessel 10 as pressurized solution is injected at the first end of blood vessel 10.

A branch clamp 95 for grasping respective branch stubs on vessel 10 extends from a body 96 mounted in a track 97 along the edge of first tray 76. Branch clamp 95 is repositionable between fixtures 82 and 83 to assist in closing off each respective branch stub.

Figure 9:
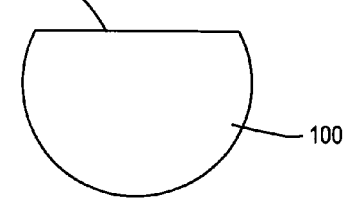
FIG. 9 is a side view of a vessel support disk.

In order to assist in identifying the length of blood vessel 10, first tray 76 includes markings 98 on its inside surface at predetermined intervals. Preferably, graduation marks may be embossed or engraved on the surface at regular intervals, such as 1 cm. Preferably, the graduation marks are associated with respective slots and the user may easily determine approximate length of the vessel in response to the markings of the respective slots containing fixtures 82 and 83. An adjustable support 100 as shown in FIG. 9 is adapted to be placed in any particular slot between first and second fixtures 82 and 83 to provide a flat surface 101 beneath vessel 10 at a point where the vessel is to be cut. Flat surface 101 provides a cutting surface at the desired position along vessel 10.

Figure 10:
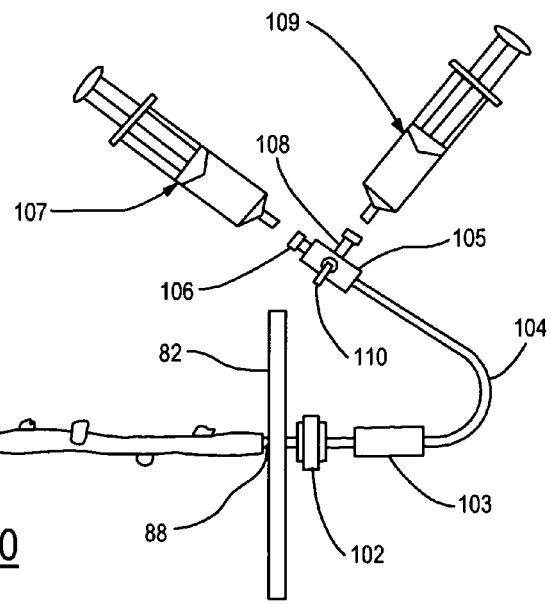
FIG. 10 is a plan view showing alternative devices for supplying pressurized fluid for leak testing.

FIG. 10 shows an alternative embodiment for providing pressurized solution to vessel 10. Fluid supply needle 88 is coupled to a luer connection 102 which is further connected to a pressure relief valve 103. A fluid conduit 104 connects relief valve 103 with a valve 105 which may be comprised of a three-way or a four-way valve, for example. A first port 106 on valve 105 is coupled to a first syringe 107. A second port 108 is coupled to a second syringe 109. A control lever 110 may be manipulated to connect the outlet of valve 105 to either one of syringes 107 or 109, so that if more than the capacity of one syringe is needed during preparation and testing of vessel 10, then it is easily obtained by the redundant syringes. The valve ports may also be comprised of "needle-free" valve ports known in the art.

In view of the foregoing, the invention provides a sterile, disposable kit to be used during surgical bypass procedures for blood vessel preparation and preservation. The kit has openable trays to provide a work surface and holder for the vessel. The kit enables pressure testing for leaks, visual inspection of the condition of the vessel, and a wet holding place for the vessel to reside until needed for surgery. Moreover, the kit provides a way to measure and cut the vessel to a desired size for the bypass graft operation.

What is claimed is:

1. Apparatus for supporting a blood vessel during processing for use in bypass graft surgery, comprising:
    a clamshell base having first and second trays latchable in a closed condition and pivotable to an open condition, wherein the first tray has a series of open slots on an interior surface, wherein each slot extends substantially transverse to the longitudinal axis of the clamshell base;
    a first fixture having a first plate positionable in any selected one of the slots, a first fitting for holding a first end of the blood vessel, and a fluid supply needle for inserting into the first end of the blood vessel; and
    a second fixture having a second plate positionable in any selected one of the slots a predetermined distance from the first fixture and having a second fitting for holding a second end of the blood vessel; and
    a liquid-retaining foam mounted in the second tray.

2. The apparatus of claim 1 wherein the first and second trays enclose a substantially cylindrical space when in the closed condition.

3. The apparatus of claim 2 wherein the first and second plates are substantially circular-disk shaped and are rotatable in their respective slots.

4. The apparatus of claim 1 wherein the first and second fittings are independently rotatable on the first and second plates, respectively, for rotating the first and second ends of the blood vessel, respectively.

5. The apparatus of claim 1 further comprising:
a fluid conduit for coupling a source of pressurized solution to the fluid supply needle so that pressurized solution can be injected into the blood vessel.

6. The apparatus of claim 5 further comprising:
a syringe coupled to the fluid conduit for providing the pressurized solution as a saline solution.

7. The apparatus of claim 5 further comprising:
a pressure gauge coupled to the fluid conduit for displaying a pressure indication.

8. The apparatus of claim 5 further comprising:
a pressure relief valve coupled to the fluid conduit for purging pressurized solution from the fluid conduit when the pressure of the pressurized solution is greater than a predetermined pressure;
wherein the apparatus is disposable.

9. The apparatus of claim 1 wherein the second fixture further comprises a hydrophilic filter for purging air from the second end of the blood vessel.

10. The apparatus of claim 1 wherein the blood vessel includes branch stubs to be closed during processing and wherein the apparatus further comprises:
a branch clamp mounted to the clamshell base and repositionable between the first and second fixtures for selectably grasping a selected branch stub.

11. The apparatus of claim 1 comprising graduation marks on the first tray associated with respective slots for determining a length of the blood vessel.

12. The apparatus of claim 1 wherein the foam is substantially semi-cylindrically shaped with a longitudinal groove for receiving the blood vessel and applying liquid stored in the foam to the blood vessel.

13. The apparatus of claim 12 wherein the foam is a biocompatible, open cell foam.

14. The apparatus of claim 1 further comprising sterile saline solution retained in the foam.

15. The apparatus of claim 1 further comprising a cutting plate insertable into a slot in the first tray, wherein the cutting plate has a flat surface positionable under the blood vessel for providing a backstop for cutting of the blood vessel.

16. The apparatus of claim 1 further comprising first and second syringes and a valve for selectably coupling either one of the first and second syringes to the fluid supply needle.

* * * * *